(12) United States Patent
Wang et al.

(10) Patent No.: US 12,253,453 B2
(45) Date of Patent: Mar. 18, 2025

(54) MULTIFUNCTIONAL VOLUMETRIC ADSORPTION TEST UNITS AND METHODS OF USING SAME

(71) Applicant: Saudi Arabian Oil Company, Dhahran (SA)

(72) Inventors: Yuguo Wang, Dhahran (SA); Md Ashraful Islam, Dhahran (SA); Ameen Alabdulaal, Inak (SA)

(73) Assignee: Saudi Arabian Oil Company, Dhahran (SA)

( * ) Notice: Subject to any disclaimer, the term of this patent is extended or adjusted under 35 U.S.C. 154(b) by 658 days.

(21) Appl. No.: 17/568,197

(22) Filed: Jan. 4, 2022

(65) Prior Publication Data

US 2023/0213430 A1    Jul. 6, 2023

(51) Int. Cl.
  *G01N 15/08* (2006.01)
  *G01K 13/024* (2021.01)
  *G01L 27/00* (2006.01)
  *G01N 33/22* (2006.01)

(52) U.S. Cl.
  CPC .......... *G01N 15/08* (2013.01); *G01K 13/024* (2021.01); *G01L 27/00* (2013.01); *G01N 2015/0873* (2013.01)

(58) Field of Classification Search
  CPC .......... G01N 15/08; G01N 2015/0873; G01N 33/225; G01K 13/024; G01L 27/00
  See application file for complete search history.

(56) References Cited

FOREIGN PATENT DOCUMENTS

| CN | 106644819 |   | 5/2017 |         |
|----|-----------|---|--------|---------|
| CN | 106644819 A | * | 5/2017 | ............... G01N 7/00 |
| CN | 106018165 |   | 6/2019 |         |
| CN | 213456540 |   | 6/2021 |         |
| SU | 1594418   |   | 9/1990 |         |

OTHER PUBLICATIONS

Gomes et al., "Experimental High-Throughput Adsorption Unit for Multi-Evaluation of Adsorbents for Gas Capture, Storage and Separation Applications," dissertation for the degree of Master of Chemical and Biochemical Engineering, NOVA University Lisbon, Apr. 2024, 76 pages.
SAIP Exam in Saudi Arabian Appln. No. 123440985, dated Jun. 19, 2024, 18 pages.

* cited by examiner

*Primary Examiner* — Eric S. McCall
*Assistant Examiner* — Anthony W Megna Fuentes
(74) *Attorney, Agent, or Firm* — Fish & Richardson P.C.

(57) ABSTRACT

Technical equilibrium can be used to measure a single gas isotherm in a relatively fast and continuous manner rather than, for example, in a batch manner. Further, an expansion vessel can be used for successive desorption a multicomponent gas in combination with determining the composition of the multicomponent gas in combination with a calculation that provides both qualitative and quantitative information about the multicomponent gas. Moreover, a multicomponent gas can be flowed through an adsorbent bed and the and the flow of the multicomponent gas flow is shut off and isolated when equilibrium is reached.

9 Claims, 8 Drawing Sheets

MULTIFUNCTIONAL VOLUMETRIC ADSORPTION TEST UNITS AND METHODS OF USING SAME

FIELD

The disclosure provides multifunctional volumetric adsorption test units and methods of using the units.

BACKGROUND

Depending on the source and geographical location of production, natural gas can contain up to 95 mole % methane ($CH_4$), with the remainder of being formed of a mixture of gases, such as carbon dioxide ($CO_2$), nitrogen ($N_2$), and small amounts of higher molecular weight hydrocarbons, such as ethane ($C_2H_6$), propane ($C_3H_8$) and butane ($C_4H_{10}$). In some cases, it is desirable to store natural gas as adsorbed natural gas, where the gas is stored on porous materials packed into a vessel at much lower pressure.

SUMMARY

The disclosure provides multifunctional volumetric adsorption test units and methods of using the units. As an example, the disclosure provides methods of measuring adsorbent helium skeletal volume for a Gibbs excess adsorption amount calculation. As another example, the disclosure provides methods of measuring a single gas Gibbs excess adsorption isotherm based on volumetric expansion and the measured adsorbent helium skeletal volume. As a further example, the disclosure provides methods of determining a multicomponent gas mixture breakthrough curve (concentration desorbed adsorbate as a function of time). As an additional example, the disclosure provides method of determining a multicomponent gas mixture adsorption isotherm. This can be based on dynamic equilibrium adsorption in flow mode at different pressures and subsequent desorption analysis of the gas composition to quantify the Gibbs excess adsorbed amount for each component of the multicomponent gas mixture.

The units can have an efficient design, which can result in reduced cost and complexity. As an example, the unit can be used to perform adsorption measurements for both a single gas and multiple gases with reduced complexity.

The methods can allow for relatively fast methods of measuring adsorption isotherms for a single gas and for gas mixtures.

The methods can allow for the relatively rapid determination of desired parameters, such as, for example, Gibbs excess adsorption isotherms for a single gas at technical equilibrium in a continuous flow mode.

The methods can use a known fixed composition of a gas mixture in a flow mode to study both the breakthrough curve and the multicomponent adsorption isotherm together.

The methods can use a successive desorption method to calculate the adsorbed amount of a mixture gases.

The methods can use continuous flow for measuring a technical equilibrium adsorption isotherm.

The methods can be used to screen adsorbents in a relatively rapid manner, e.g., for use in ANG technologies.

In some embodiments, technical equilibrium can be used to measure a single gas isotherm in a relatively fast and continuous manner, compared, for example, to using batch method.

In certain embodiments, an expansion vessel is used for successive desorption of a multicomponent when determining the composition of the multicomponent gas to calculate both qualitative and quantitative information about the multicomponent gas. In other words, both the identity of each gas that was adsorbed and the amount of each gas that was adsorbed can be determined.

In some embodiments, a multicomponent gas is flowed through an adsorbent bed and the flow of the multicomponent gas flow is shut off and isolated when equilibrium is reached. Optionally, this method can be combined with (e.g. performed in advance of) the method disclosed in the preceding paragraph.

In certain embodiments, the units and methods can be advantageously implemented in relation to ANG. In ANG, microporous adsorbents can offer relatively high energy density and relatively high volume to volume storage capacity compared with compressed natural gas (e.g., at a pressure of above 200 bars). Often, in ANG technology it is preferable to use a volume to volume adsorption capacity measurement rather than gravimetric methods, particularly for adsorbents having a low packing density and/or where the vessel size is limited. Because natural gas is a mixture of gases, it can be desirable to determine the multicomponent adsorption capacity to characterize the adsorbent for storage and separation purposes.

In an aspect, the disclosure provides a method that includes: controlling flow of a single component gas to a vessel so that so that the gas adsorbs to an adsorbent within an interior of the vessel; after a predetermined pressure of the single component gas within the interior of the vessel is reached, stopping the flow of the single component gas to the vessel; and determining an amount of the single component gas adsorbed to the adsorbent at the predetermined pressure.

The method can further include repeatedly performing the controlling, stopping and determining steps to provide an adsorption isotherm for the single component gas.

The method can further include using a mass flow controller to control the flow of the single component gas so that the flow has a Deborah number of at most one.

The method can further include, while flowing the single component gas to the vessel, measuring the pressure within the interior of the vessel.

The method can further include, while flowing the single component gas to the interior of the vessel, measuring a temperature within the interior of the vessel.

The method can further include: during the controlling step, using a mass flow controller to control the flow of the single component gas so that the flow has a Deborah number of at most one and measuring the pressure within the interior of the vessel; and repeatedly performing the controlling, stopping and calculating steps to provide data comprising a plurality of determined Gibbs excess amounts of adsorption of the single component gas on the adsorbent, wherein the single component gas comprises methane.

In an aspect, the disclosure provides a unit that includes: a vessel comprising an adsorbent; a pressure monitor configured to measure a pressure within the interior of the vessel; a gas source configured to provide a single component gas; and a mass flow controller between the gas source and the interior of the vessel. The mass flow controller is configured to control a flow of the single component gas from the gas source to the interior of the vessel.

The unit can further include a controller configured to control the mass flow controller so that the flow of the single component gas from the gas source to the interior of the adsorption vessel has a Deborah number of at most one. The controller can be configured to turn off the mass flow controller when the pressure monitor measures that the interior of the vessel has reached a predetermined pressure.

The unit can further include a temperature monitor configured to measure a temperature within the interior of the vessel.

In an aspect, the disclosure provides a method that includes: a) monitoring temperature pressure within an interior of an adsorption vessel and an interior of an expansion vessel while a gas mixture flows from the interior of the adsorption vessel to the interior of the expansion vessel, the adsorption vessel comprising an adsorbent, the gas mixture comprising a first gas and a second gas different from the first gas; b) when the pressure of the gas mixture in the adsorption vessel is the same as the pressure of the gas mixture, stopping the flow of the gas mixture from the interior of the adsorption vessel to the interior of the expansion vessel; c) after b), flowing the gas mixture from the interior of the expansion vessel to an analyzer to analyze the composition of the gas mixture after; and d) based on c), determining an amount of the first gas that was adsorbed on the adsorbent at the pressure in b) and determining an amount of the first gas that was adsorbed on the adsorbent at the pressure b).

The method can further include repeatedly performing a)-d), and, based on data collected when performing c) each time, determining an adsorption isotherm for each of the first and second gases.

The method can further include, before a): e) while preventing the gas mixture from flowing to the interior of the expansion vessel, providing the gas mixture to the interior of the adsorption vessel while monitoring a composition of gases flowing from the interior of the adsorption vessel to the analyzer; and f) when the analyzer determines that the composition of the gases from the interior of the adsorption vessel is stable, stopping the flow of gases from the interior of the adsorption vessel to the analyzer. The method can further include, during e) controlling a flow rate of the gases from the interior of the adsorption vessel to the analyzer.

The method can further include, before a): e) while preventing the gas mixture from flowing to the interior of the expansion vessel, providing the gas mixture to the interior of the adsorption vessel while: i) controlling a flow rate of the gases from the interior of the adsorption vessel to the analyzer; and ii) monitoring a composition of gases flowing from the interior of the adsorption vessel to the analyzer; and f) when the analyzer determines that the composition of the gases from the interior of the adsorption vessel is stable, stopping the flow of gases from the interior of the adsorption vessel to the analyzer. In addition, the method can include repeatedly performing a)-f); and based on data collected when performing c) each time, determining an adsorption isotherm for each of the first and second gases, wherein the gas mixture comprises methane and ethane.

In an aspect, the disclosure provides a unit, including: an adsorption vessel having an interior comprising adsorbent; a pressure monitor configured to measure a pressure of the interior of the adsorption vessel; an expansion vessel having an interior; a pressure monitor configured to measure a pressure of the interior of the adsorption vessel; and a gas analyzer. In a first mode, the interior of the adsorption vessel is in fluid communication with the interior of the expansion vessel, the interior of the adsorption of vessel is not in fluid communication with the gas analyzer, and the interior of the expansion vessel is not in fluid communication with the gas analyzer. In a second mode, the interior of the adsorption vessel is not in fluid communication with the interior of the expansion vessel, the interior of the adsorption of vessel is not in fluid communication with the gas analyzer, and the interior of the expansion vessel is in fluid communication with the gas analyzer.

The unit can further include: a first valve configured to control fluid communication between: 1) the interior of the adsorption vessel and the interior of the expansion vessel; and 2) the interior of the adsorption vessel and the gas analyzer; and a second valve configured to control fluid communication between the interior of the expansion vessel and the gas analyzer.

The unit can further include a regulator configured to control a gas flow from the interior of the adsorption vessel.

The unit can be configured so that, in a third mode, the interior of the adsorption vessel is in not fluid communication with the interior of the expansion vessel, the interior of the adsorption of vessel is in fluid communication with the gas analyzer, and the interior of the expansion vessel is not in fluid communication with the gas analyzer.

The unit can further include: a first valve configured to control fluid communication between: 1) the interior of the adsorption vessel and the interior of the expansion vessel; and 2) the interior of the adsorption vessel and the gas analyzer; a second valve configured to control fluid communication between the interior of the expansion vessel and the gas analyzer; and a regulator configured to control a gas flow from the interior of the adsorption vessel. In a third mode, the interior of the adsorption vessel is in not fluid communication with the interior of the expansion vessel, the interior of the adsorption of vessel is in fluid communication with the gas analyzer, and the interior of the expansion vessel is not in fluid communication with the gas analyzer.

DETAILED DESCRIPTION

The disclosure provides multifunctional volumetric adsorption test units and methods of using the units.

Figure 1:
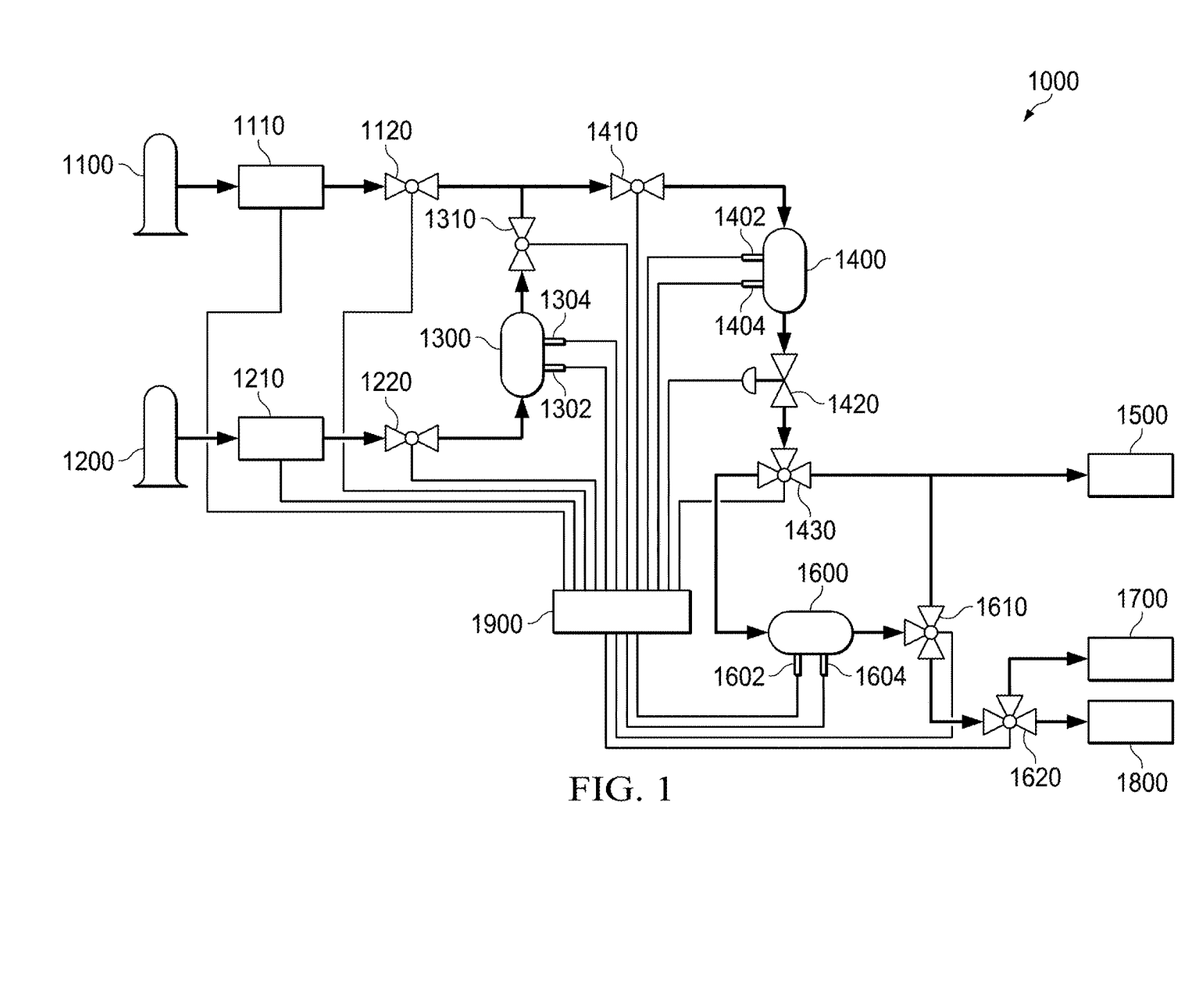
FIG. 1 schematically shows a multifunctional volumetric adsorption test unit.

FIG. 1 schematically shows a multifunctional volumetric adsorption test unit 1000 that includes a gas source 1100 containing methane and ethane, a gas source 1200, a storage vessel 1300, an adsorption vessel 1400 containing an adsorbent such as activated carbon, a gas chromatograph 1500, an expansion vessel 1600, a vent 1700 and a vacuum pump 1800. The unit 1000 also includes mass flow controllers 1110 and 1210, bypass valves 1120, 1220, 1310 and 1410, a back pressure regulator 1420, and three-way valves 1430, 1610 and 1620. The unit 1000 further includes a temperature monitor 1302 and a pressure monitor 1304 to monitor the temperature and pressure, respectively, of the interior of the storage vessel 1300. In addition, the unit 1000 includes a temperature monitor 1402 and a pressure monitor 1404 to monitor the temperature and pressure, respectively, of the interior of the adsorption vessel 1400. Moreover, the unit 1000 includes a temperature monitor 1602 and a pressure monitor 1604 to monitor the temperature and pressure, respectively, of the interior of the expansion vessel 1600. In addition, the unit 1000 includes a controller 1900 which is connected to the mass flow controllers 1110 and 1210, the bypass valves 1120, 1220, 1310 and 1410, the back-pressure regulator 1420, the three-way valves 1430, 1610 and 1620, and the monitors 1302, 1304, 1402, 1404, 1602 and 1604 to control operation of these components. Additionally, or alternatively, the unit 1000 can be configured so that one or more of these components can be manually controlled. In some embodiments, the unit 1000 does not include the controller 1900. In such embodiments, each of the components can be manually controlled. In some embodiments, the temperature of the storage vessel 1300, the adsorption vessel 1400 and/or the expansion vessel 1600 can be stabilized. For example, one or more of these vessels can be maintained in a thermal bath. In some embodiments, such a thermal bath is a liquid, such as an oil, that surrounds the exterior of a given vessel (e.g., an oil in a jacket that surrounds the vessel). In certain embodiments, the thermal bath can be a gas (e.g., air).

Figure 2:
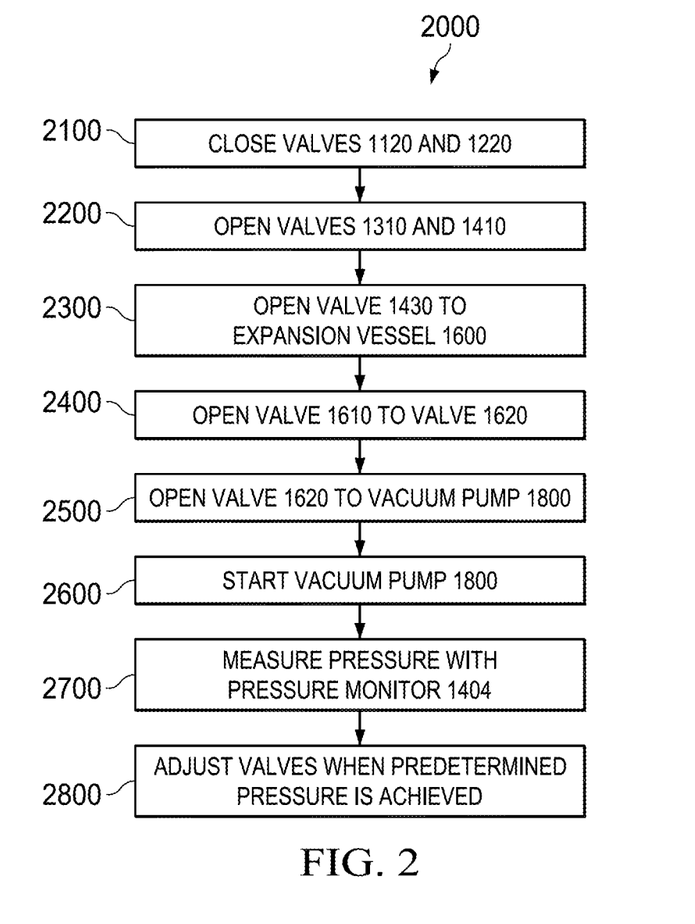
FIG. 2 is a flow chart of a method of evacuating a multifunctional volumetric adsorption test unit.

FIG. 2 is a flow chart of a method 2000 of evacuating the unit 1000. In step 2100, the bypass valves 1120 and 1220 are closed. In step 2200, the bypass valves 1310 and 1410 are opened. In step 2300, the three-way valve 1430 is opened to the direction of the expansion vessel 1600. In step 2400, the three-way valve 1610 is opened to the direction of the three-way valve 1620. In step 2500, the three-way valve 1620 is opened to the direction of the vacuum pump 1800. In step 2600, the vacuum pump 1800 is started. In step 2700, the pressure in the adsorption vessel 1400 is measured using the pressure monitor 1404. In step 2800, when the pressure monitor 1404 shows a predetermined pressure (e.g., minus one bar), valve 1310 is closed, three-way valve 1430 is turned to the direction of the adsorption vessel 1400, the three-way valve 1610 is turned to the direction of the expansion vessel 1600, and the three-way valve 1620 is turned to the direction of the three-way valve 1610.

Figure 3:
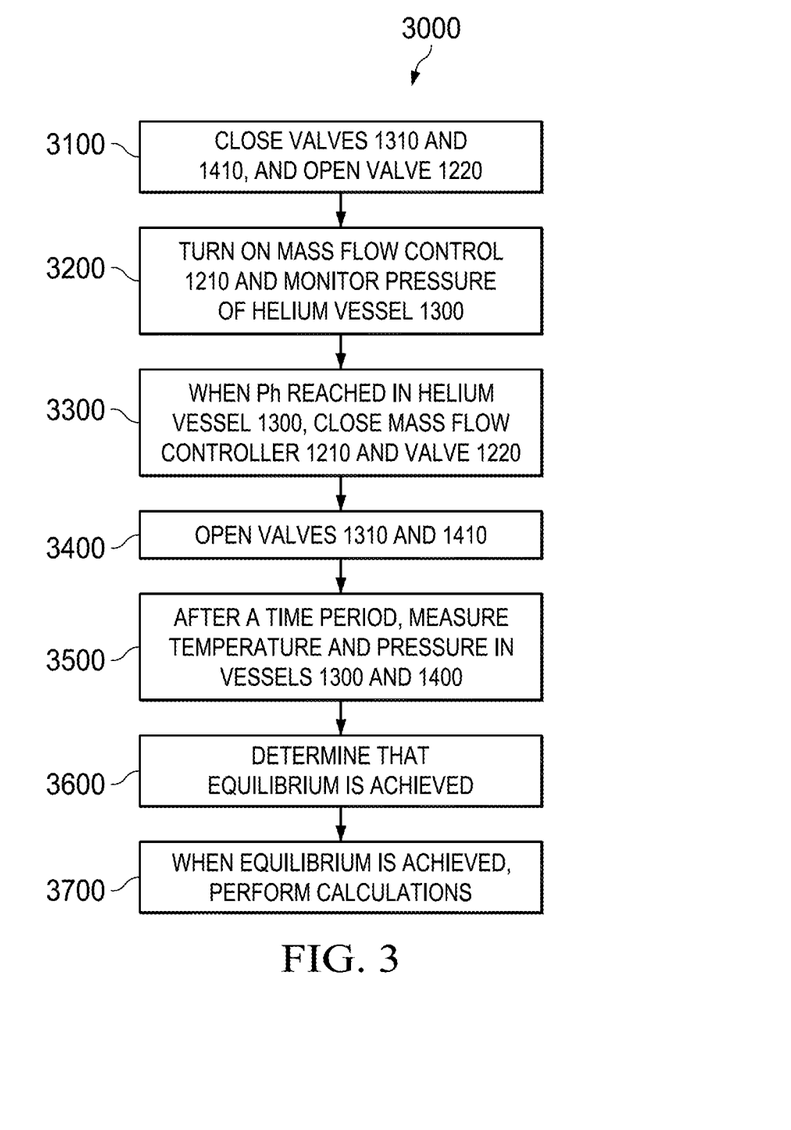
FIG. 3 is a flow chart of a method of performing an adsorbent helium volume measurement.

FIG. 3 is a flow chart of a method 3000 of performing an adsorbent helium volume measurement after evacuation of the unit 1000 according to the method 2000. This measurement can be used to determine the skeletal volume ($V_s$) of the adsorbent (e.g., activated carbon) within the adsorption vessel 1400. As explained below, this parameter can be used in measurements of a single gas adsorption isotherm, a technical equilibrium adsorption isotherm, an adsorption isotherm for a gas mixture.

In step 3100 of method 3000, the bypass valves 1310 and 1410 are closed, and the bypass valve 1220 is opened. In step 3200, the mass flow control 1210 is turned on and the storage vessel 1300 is charged with helium gas while the pressure monitor 1304 measures the pressure of helium gas in the storage vessel 1300. In step 3300, when the pressure monitor 1304 shows that the storage vessel 1300 has reached a desired gas pressure $P_h$, the mass flow controller 1210 is closed and the bypass valve 1220 is closed. In step 3400, the bypass valves 1310 and 1410 are opened, and helium gas flows from the storage vessel 1300 to the adsorption vessel 1400. In step 3500, after an appropriate period of time (e.g., 20 minutes), the temperature and pressure in vessels 1300 and 1400 are measured with monitors 1302, 1304, 1402 and 1404. In step 3600, it is determined that equilibrium is achieved when the temperature measured by the monitor 1302 is the same as the temperature measured by the monitor 1402 (which is the equilibrium temperature $T_e$ and pressure $P_e$), and when the pressure measured by the monitor 1304 is the same as the pressure measured by the monitor 1404 (which is the equilibrium pressure $P_e$). In step 3700, when equilibrium is achieved, the following calculations are performed.

$$Nh = \frac{Ph * Vh}{R * T * Z(Ph, T)} \quad (1)$$

$$Vs = Vh + Vav - \frac{Nh * R * Te * Z(Pe, Te)}{Pe} \quad (2)$$

$N_h$ is the moles of helium gas in the storage vessel 1300, $P_h$ is a desired gas pressure (see step 3300), $V_h$ is the volume of the storage vessel 1300, R is the universal gas constant (8.314 J/molK), T is the temperature measured by the temperature monitor 1302, Z is the compressibility factor of helium gas (a function of pressure and temperature), $V_s$ is the skeletal volume of the adsorbent (e.g., activated carbon) within the adsorption vessel 1400, $V_{av}$ is the volume of the adsorption vessel 1400, $T_e$ is the temperature (see step 3600), and $P_e$ is the equilibrium pressure (see step 3600).

Figure 4:
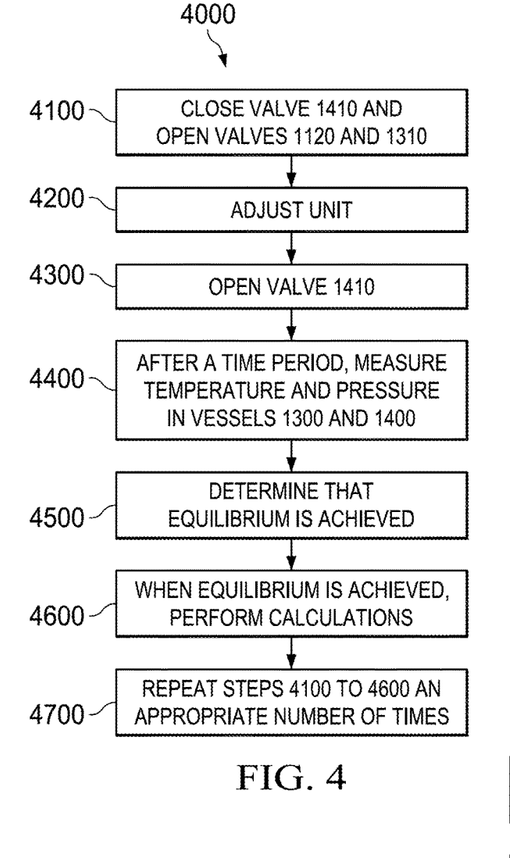
FIG. 4 is a flow chart for a method performing a single gas isotherm measurement.

FIG. 4 is a flow chart for a method 4000 performing a single gas isotherm measurement after evacuation of the unit 1000 according to the method 2000. In step 4100, valve 1410 is closed and valves 1120 and 1310 are opened. In step 4200, the mass flow controller 1110 is turned on so that a single gas (e.g., methane) flows from the gas source 1100 to the storage vessel 1300 to reach a desired pressure $P_h$ at a temperature $T_h$ in the storage vessel 1300, after which the mass flow controller 1110 and the valve 1120 are turned off, and the equilibrium pressure and temperature of the storage vessel 1300 are measured as $P_h$ and $T_h$ using the monitors 1302 and 1304, respectively. In step 4300, the valve 1410 is opened so that the gas (e.g., methane) flows to the adsorption vessel 1400. In step 4400, after an appropriate period of time (e.g., 20 minutes), the temperature and pressure in vessels 1300 and 1400 are measured with monitors 1302, 1304, 1402 and 1404. In step 4500, it is determined that equilibrium is achieved when the temperature measured by the monitor 1302 is the same as the temperature measured by the monitor 1402 (which is the equilibrium temperature Te), and when the pressure measured by the monitor 1304 is the same as the pressure measured by the monitor 1404 (which is the equilibrium pressure Pe). In step 4600, when equilibrium is achieved, the following calculations are performed.

$$N_h = \frac{P_h * V_h}{R * T * Z(P_h, T)} \quad (3)$$

$$NGE = N_h - \frac{N_h * R * Te * Z(Pe, Te)}{(V_h + V_{av} - V_s)} \quad (4)$$

NGE is the Gibbs excess amount of adsorption on the adsorbent. Conceptually, NGE relates to the excess of amount of the single gas (e.g., methane) adsorbed on the adsorbent within the adsorption vessel 1400. If the adsorbent mass is $M_{ad}$, the bulk density is $M_{ad}/V_{av}$ (assuming the adsorption vessel 1400 is filled with adsorbent), and the adsorbent has a skeletal volume of $V_s$. Then, NGE can be converted to volume to volume adsorption (VGE) using the following equation 5 at standard temperature and pressure ($T_s=25°$ C. and $P_s=1$ bar).

$$VGE = \frac{NGE * R * T_s * Z(T_s, P_s)}{P_s * V_{av}} \quad (5)$$

Figure 5:
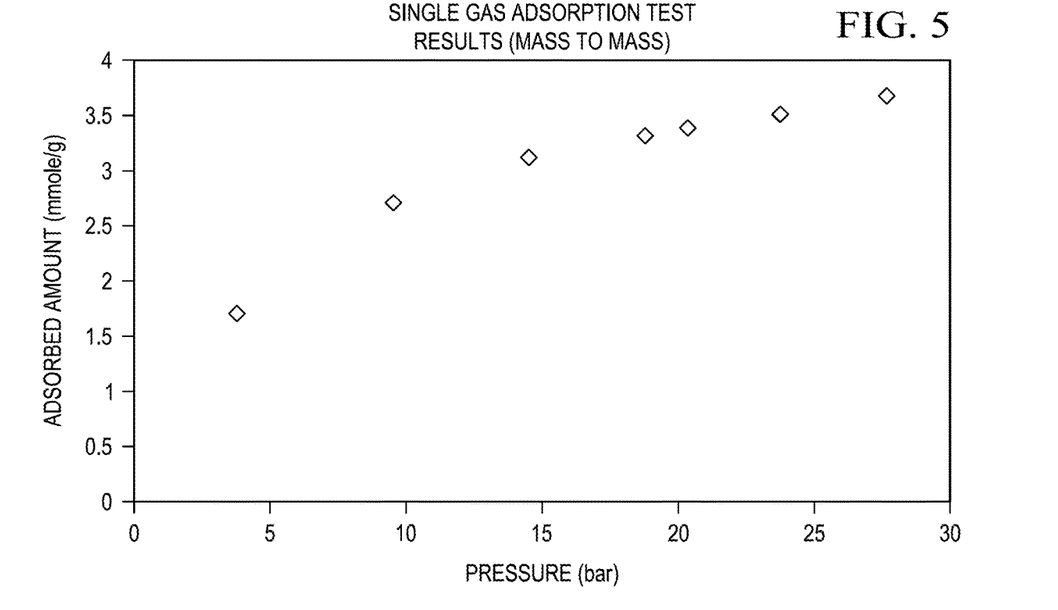
FIG. 5 is a graph showing a single adsorption isotherm (mass to mass).
Figure 6:
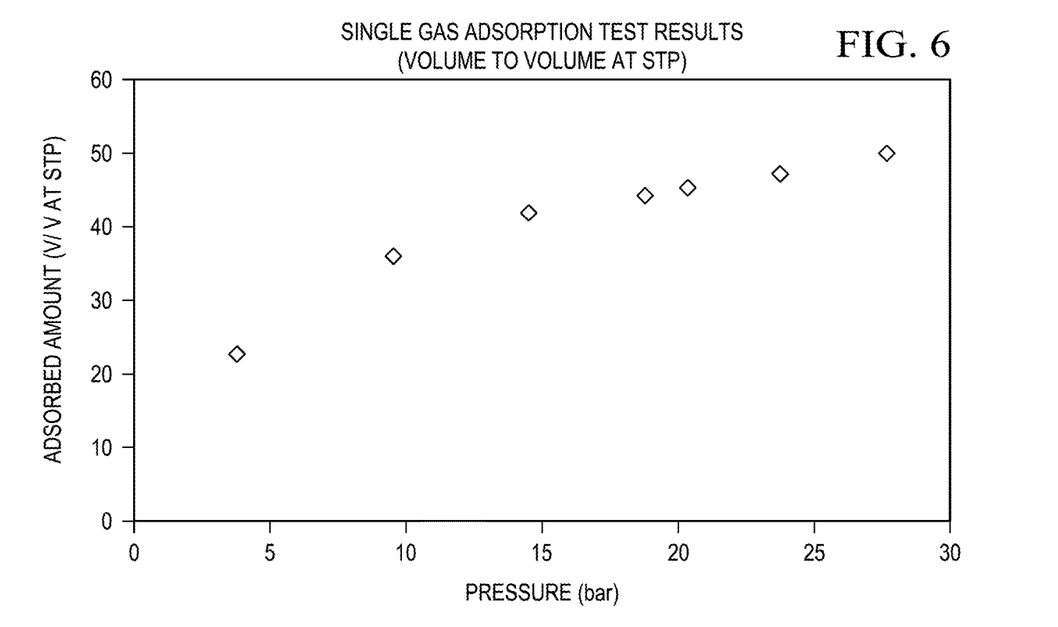
FIG. 6 is a graph showing a single gas adsorption isotherm (volume to volume at standard temperature and pressure).

In step 4700, the steps 4100 to 4600 are repeated a desired number of times to collect data for NGE as a function of $P_e$ and VGE as a function of $P_e$. Plots of the collected data can subsequently be prepared. FIG. 5 is a graph showing the mass to mass adsorption isotherm for methane at 10° C. for an activated carbon based on the calculated NGE as a function of pressure. Using equation 5, the adsorption amount can be converted to volume to volume ratio, which means the equivalent volume of methane at STP (standard temperature and pressure) to the packing volume of the adsorbent. This is shown in FIG. 6.

It can take an undesirably long period of time to reach thermodynamic equilibrium. We therefore introduce the concept of "technical equilibrium" which we define as a state in which the relative uptake ($\Delta m/m$) of mass at total mass (m) due to adsorption is less than an appropriate value ($\varepsilon$) (e.g., $\varepsilon=10^{-5}$) within an appropriate period of time ($\Delta t$) (e.g., $\Delta t=30$ minutes). The data allow, together with cycle periods ($t_c$) of an industrial process, for defining characteristic Deborah numbers for the process as shown by the following equation.

$$De = \frac{\Delta m}{\Delta t}\left(\frac{t_c}{m}\right) \quad (6)$$

This allows for approximately describing the "distance" of an actual state of an adsorption system from its thermodynamic equilibrium state at given temperatures and pressure. As an example, as De approaches zero ($D_e \to 0$), the process is near equilibrium. As another example, when De is equal to or greater than 100 ($D_e \geq 100$), substantially non-equilibrium phenomena in heat and mass transfer are, in general, to be taken into account.

Figure 7:
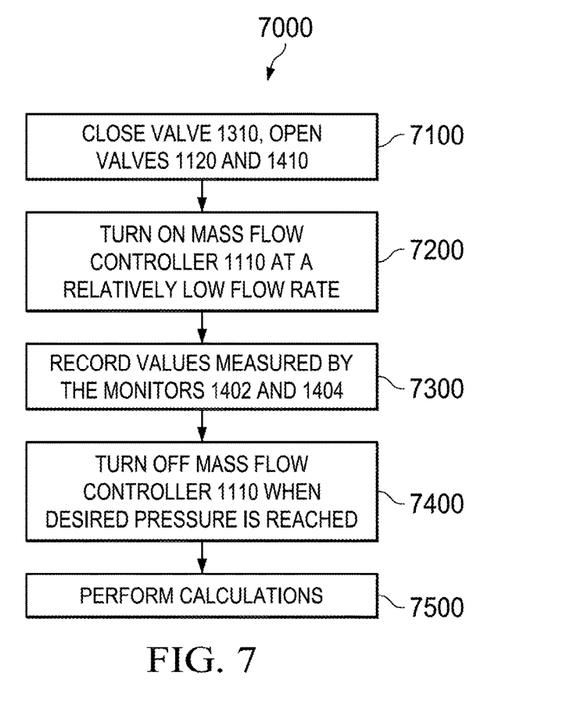
FIG. 7 is a flow chart for a process for obtaining technical equilibrium adsorption isotherm data.

FIG. 7 is a flow chart for a process 7000 for obtaining a single gas technical equilibrium adsorption isotherm data after evacuation of the unit 1000 according to the method 2000. In step 7100, the bypass valve 1310 is closed, and the bypass valves 1120 and 1410 are opened. In step 7200, the mass flow controller 1110 is turned on at a relatively low flow rate such that De is less than or equal to one ($D_e \leq 1$) with a single gas (e.g., methane) flowing from the gas source 1100 to the adsorption vessel 1400. In step 7300, the values measured by the monitors 1402 and 1404 are recorded with a time interval of $D_e \leq 1$ as Pe and Te. In step 7400, the mass flow controller 1110 is turned off when the desired pressure is reached. In step 7500, the following calculations are performed.

$$NGE = N_{mfc} - \frac{N_{mfc} * R * Te * Z(Pe, Te)}{(V_h + V_{av} - V_s)} \quad (7)$$

$N_{mfc}$ is the moles of gas (e.g., methane) flowing through the mass flow controller 1110 at different times. The Gibbs excess amount of adsorption on adsorbent is calculated using the following equation.

$$VGE = \frac{NGE * R * T_s * Z(T_s, P_s)}{P_s * V_{av}} \quad (8)$$

Figure 8:
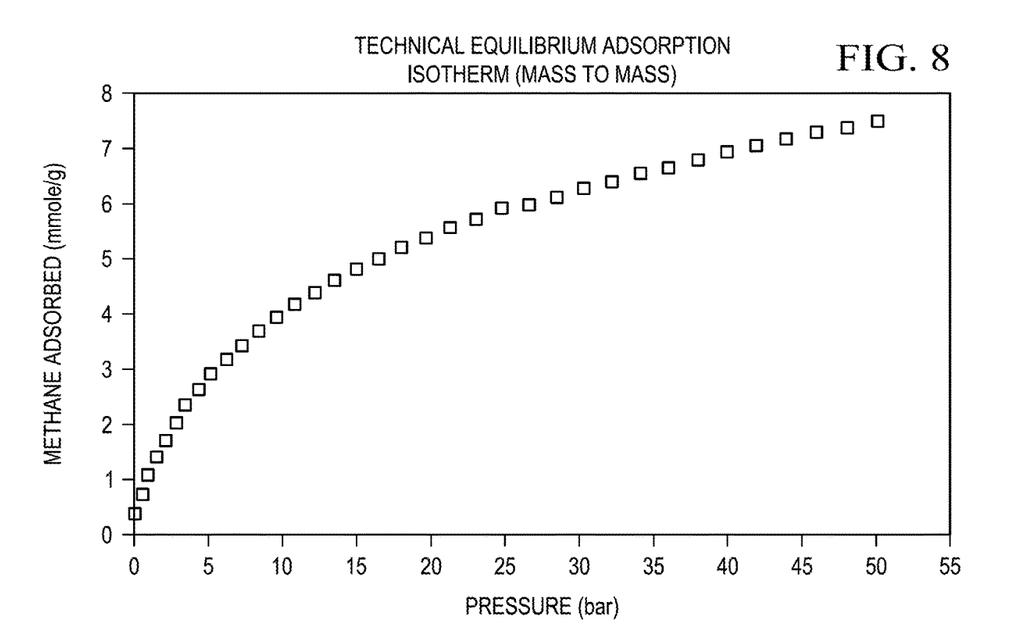
FIG. 8 shows a technical equilibrium adsorption isotherm (mass to mass).
Figure 9:
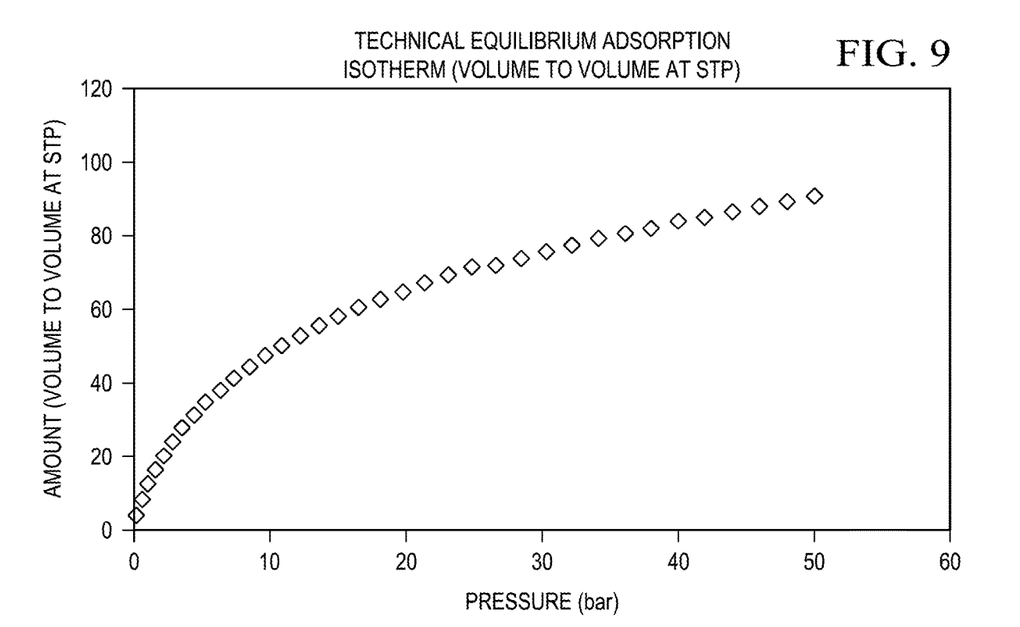
FIG. 9 shows a technical equilibrium adsorption isotherm (volume to volume at standard temperature and pressure).

FIG. 8 shows the data for the Gibbs excess adsorption isotherm at 21° C. for an activated carbon adsorbent (mass to mass adsorption isotherm) based on the calculated NGE. The adsorption amount can be converted to a volume to volume ratio using equation 8, which means the equivalent volume of methane at standard temperature and pressure to the packing volume of the adsorbent. This is shown in FIG. 9.

Figure 10:
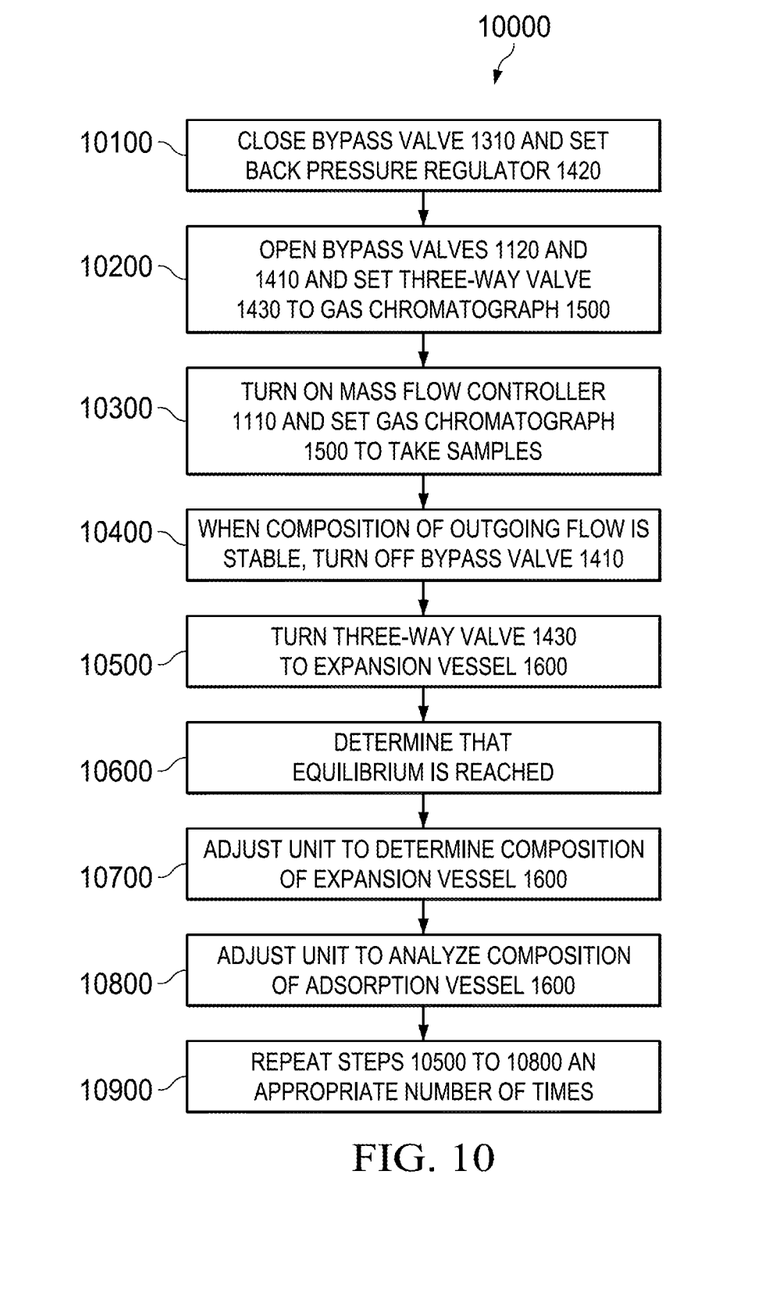
FIG. 10 is a flow chart of a method of performing a gas mixture adsorption isotherm data measurement.

FIG. 10 is a flow chart for a process 10000 for performing a gas mixture adsorption isotherm data measurement after evacuation of the unit 1000 according to the method 2000. In step 10100, the bypass valve 1310 is closed, and the back pressure regulator 1420 is set to a desired pressure $P_e$. In step 10200, the bypass valves 1120 and 1410 are opened and the three-way valve 1430 is set to the direction of the gas chromatograph 1500. In step 10300, the mass flow controller 1110 is turned on so that a gas mixture (e.g., containing methane and ethane) flows from the gas source 1000, and the gas chromatograph 1500 is set to take samples at desired time periods (e.g., every two minutes). When the desired pressure is reached, the gas mixture will flow through the back pressure regulator 1420 and the three-way valve 1430 to the gas chromatograph 1500 for compositional analysis. In step 10400, when the composition of the outgoing flow as measured with the gas chromatograph 1500 is stable and same as the gas composition in 1100, the bypass valve 1410 is turned off. In step 10500, the three-way valve 1430 is turned to the direction of the expansion vessel 1600 so that the gas mixture flows from the adsorption vessel 1400 to the expansion vessel 1600. In step 10600, it is determined that equilibrium is reached when the temperature measured by the monitor 1402 is the same as the temperature measured by the monitor 1602 (which is the equilibrium temperature $T_e$), and when the pressure measured by the monitor 1404 is the same as the pressure measured by the monitor 1604 (which is the equilibrium pressure $P_e$), at which point the three-way valve 1430 is turned to a neutral direction. In step 10700, the composition of the expansion vessel 1600 is analyzed by switching the three-way valve 1610 to the direction of the gas chromatograph 1500 while the three-way valve 1620 is in a neutral position. In step 10800, after the analysis in step 10700, the three-way valves 1610 and 1620 are turned to the vacuum pump 1700, and the expansion vessel 1400 is vacuumed. In step 10900, steps 10500 to 10800 are repeated an appropriate number of times (e.g., five or six times) to repeatedly to complete the analysis of the gas in the adsorption vessel 1400.

For a binary mixture of gases C1 and C2 (C1 for methane, C2 for ethane), adsorption of the gas mixture can be calculated as follows. The feed gas mixture has a mole % of C1 that is x, and a mole % of C2 that is y, where x+y=1.0. C1 and C2 reach dynamic equilibrium at the pressure of $P_e$, and $V_s$ is the skeletal volume of the adsorbent. The mass balance of the successive desorption will give the following equation for C1. C2 has the same equation but with its corresponding parameters.

$$\frac{((V_{av} - V_s) \times P_e \times C1)}{Z_{e1} \times R \times T_e} + nC1_{ad} = \sum_{1}^{M} \frac{(V_{ev} \times P_{dk} \times C_{k1})}{(Z_{dk1}) \times R \times T_k} \quad (9)$$

$V_{av}$ is the adsorption vessel volume, $P_e$ is the adsorption dynamic equilibrium pressure, C1 is the fixed input mole % of methane, $Z_{e1}$ is the compressibility factor, $T_e$ is the dynamic equilibrium temperature, $nC1_{ad}$ is the adsorbed amount of methane, $V_{ev}$ is the expansion vessel volume, $P_{dk}$ is the pressure of the expansion equilibrium pressure for the kth expansion, k is from 1 to M (total number of expansion, which is greater than 10), $C_{k1}$ is the mole % of methane in the expansion vessel, $Z_{dk1}$ is the compressibility factor of methane in the expansion vessel, and $T_k$ is the kth expansion equilibrium temperature.

Figure 11:
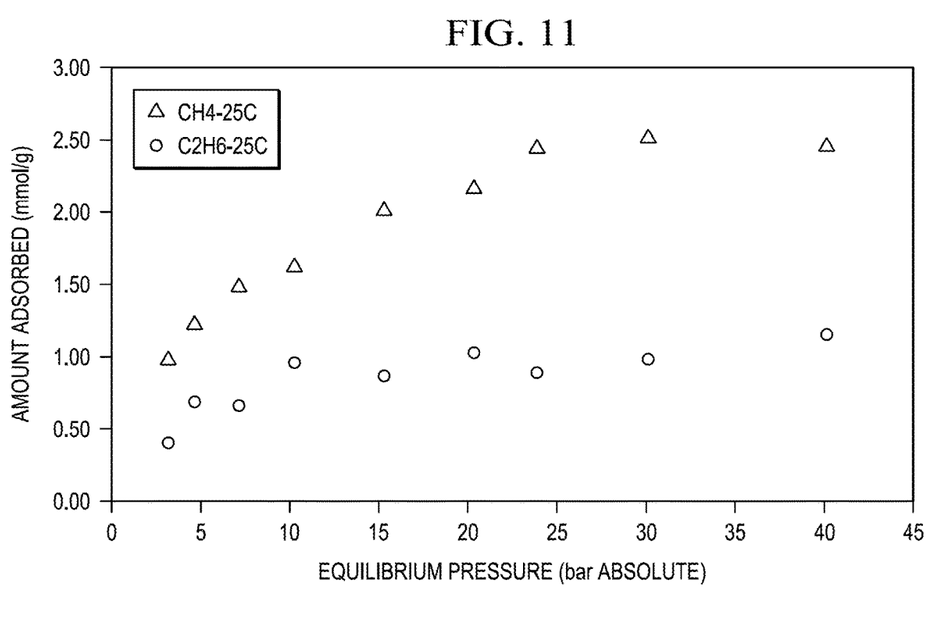
FIG. 11 is a binary mixture adsorption isotherm.
Figure 12:
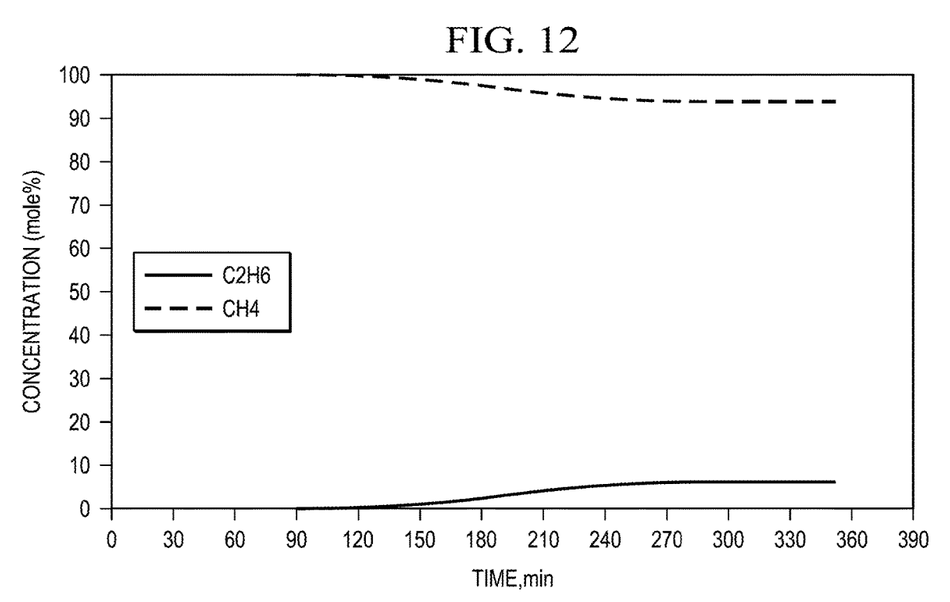
FIG. 12 is a breakthrough curve of dynamic adsorption of a binary gas mixture.

FIG. 11 is the binary mixture adsorption isotherm for methane and ethane with a composition of 93.5 of methane and 6.5% of ethane at 25° C. on activated carbon. FIG. 12 is the breakthrough curve of dynamic adsorption of C1/C2 (93.5%/6.5%) at 25° C. on an activated carbon.

Implementations of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible program carrier for execution by, or to control the operation of, a processing device. Alternatively or in addition, the program instructions can be encoded on a propagated signal that is an artificially generated signal, e.g., a machine-generated electrical, optical, or electromagnetic signal that is generated to encode information for transmission to suitable receiver apparatus for execution by a processing device. A machine-readable medium can be a machine-readable storage device, a machine-readable storage substrate, a random or serial access memory device, or a combination of one or more of them.

The term "processing device" encompasses all kinds of apparatus, devices, and machines for processing information, including by way of example a programmable processor, a computer, or multiple processors or computers. The apparatus can include special purpose logic circuitry, e.g., an FPGA (field programmable gate array) or an ASIC (application-specific integrated circuit) or RISC (reduced instruction set circuit). The apparatus can also include, in addition to hardware, code that creates an execution environment for the computer program in question, e.g., code that constitutes processor firmware, a protocol stack, an information base management system, an operating system, or a combination of one or more of them.

A computer program (which may also be referred to as a program, software, a software application, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or information (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input information and generating output. The processes and logic flows can also be performed by, and apparatus can also be implemented as, special purpose logic circuitry, e.g., an FPGA (field programmable gate array) or an ASIC (application-specific integrated circuit) or RISC.

Computers suitable for the execution of a computer program include, by way of example, general or special purpose microprocessors or both, or any other kind of central processing unit. Generally, a central processing unit will receive instructions and information from a read-only memory or a random access memory or both. The essential elements of a computer are a central processing unit for performing or executing instructions and one or more memory devices for storing instructions and information. Generally, a computer will also include, or be operatively coupled to receive information from or transfer information to, or both, one or more mass storage devices for storing information, e.g., magnetic, magneto-optical disks, or optical disks. However, a computer need not have such devices. Moreover, a computer can be embedded in another device, e.g., a mobile telephone, a smartphone or a tablet, a touch-screen device or surface, a personal digital assistant (PDA), a mobile audio or video player, a game console, a Global Positioning System (GPS) receiver, or a portable storage device (e.g., a universal serial bus (USB) flash drive), to name just a few.

Computer-readable media (e.g., one or more machine readable hardware storage devices) suitable for storing computer program instructions and information include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and (Blue Ray) DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this specification can be implemented in a computing system that includes a back-end component, e.g., as an information server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital information communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other. In another example, the server can be in the cloud via cloud computing services.

While this specification contains many specific implementation details, these should not be construed as limitations on the scope of any of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

While certain embodiments have been described, the disclosure is not limited to such embodiments.

As an example, while activated carbon has been described as an adsorbent, other adsorbents may be used. Examples of such adsorbents include molecular sieves, zeolite templated carbon, MOFs, COFs and the like.

As another example, although embodiments have been described in which technical equilibrium adsorption isotherm data is obtained for methane, such data may also be obtained for other gases. Examples of such gases include $CO_2$, $H_2$, $N_2$ and the like.

As a further example, while embodiments have been described that relate to ANG technology, the units and methods can be used with other technologies. Examples of such technologies include pressure swing adsorption for hydrogen separation, temperature swing for natural gas dehydration, and hydrogen storage for mobile applications.

As another example, combinations of the disclosed embodiments are possible.

Other embodiments are encompassed by the claims.

What is claimed is:

1. A method, comprising: controlling flow of a single component gas to a vessel so that so that the gas adsorbs to an adsorbent within an interior of the vessel; after a predetermined pressure of the single component gas within the interior of the vessel is reached, stopping the flow of the single component gas to the vessel; determining an amount of the single component gas adsorbed to the adsorbent at the predetermined pressure; during the controlling step, using a mass flow controller to control the flow of the single component gas so that the flow has a Deborah number of at most one and measuring the pressure within the interior of the vessel; and repeatedly performing the controlling, stopping and determining steps to provide data comprising a plurality of determined Gibbs excess amounts of adsorption of the single component gas on the adsorbent, wherein the single component gas comprises methane.

2. The method of claim 1, further comprising repeatedly performing the controlling, stopping and determining steps to provide an adsorption isotherm for the single component gas.

3. The method of claim 1, further comprising using a mass flow controller to control the flow of the single component gas so that the flow has a Deborah number of at most one.

4. The method of claim 1, further comprising, while flowing the single component gas to the vessel, measuring the pressure within the interior of the vessel.

5. The method of claim 4, further comprising, while flowing the single component gas to the interior of the vessel, measuring a temperature within the interior of the vessel.

6. A unit, comprising: a vessel comprising an adsorbent; a pressure monitor configured to measure a pressure within an interior of the vessel; a gas source configured to provide a single component gas; a mass flow controller between the gas source and the interior of the vessel, wherein the mass flow controller is configured to control a flow of the single component gas from the gas source to the interior of the vessel; and a controller configured to determine a plurality of Gibbs excess amounts of adsorption of the single component gas on the adsorbent.

7. The unit of claim 6, further comprising the controller configured to control the mass flow controller so that the flow of the single component gas from the gas source to the interior of the adsorption vessel has a Deborah number of at most one.

8. The unit of claim 7, wherein the controller is configured to turn off the mass flow controller when the pressure monitor measures that the interior of the vessel has reached a predetermined pressure.

9. The unit of claim 6, further comprising a temperature monitor configured to measure a temperature within the interior of the vessel.

* * * * *

UNITED STATES PATENT AND TRADEMARK OFFICE
CERTIFICATE OF CORRECTION

| | | |
|---|---|---|
| PATENT NO. | : 12,253,453 B2 | Page 1 of 1 |
| APPLICATION NO. | : 17/568197 | |
| DATED | : March 18, 2025 | |
| INVENTOR(S) | : Yuguo Wang, Md Ashraful Islam and Ameen Alabdulaal | |

It is certified that error appears in the above-identified patent and that said Letters Patent is hereby corrected as shown below:

On the Title Page

Column 2, Line 9, (57) Abstract, please replace "and the and the" with -- and the --.

In the Claims

In Column 12, Line 14, Claim 1, please replace "so that so that" with -- so that --.

Signed and Sealed this
Thirteenth Day of May, 2025

Coke Morgan Stewart
*Acting Director of the United States Patent and Trademark Office*